United States Patent
Kataoka et al.

Patent Number: 6,129,721
Date of Patent: Oct. 10, 2000

[54] MEDICAL LASER TREATMENT DEVICE AND LASER PROBE FOR THE SAME

[75] Inventors: Kenzo Kataoka; Masaki Odaka; Akira Yuba; Koichi Yamazaki, all of Kyoto; Takashi Tsumanuma, Sakura; Keiji Kaneda, Chiba, all of Japan

[73] Assignees: J. Morita Manufacturing Corporation, Kyoto; Fujikura Ltd., Tokyo, both of Japan

[21] Appl. No.: 09/089,176

[22] Filed: Jun. 2, 1998

[30] Foreign Application Priority Data

Jun. 4, 1997 [JP] Japan .................................. 9-146803

[51] Int. Cl.⁷ .................................................. A61B 17/36
[52] U.S. Cl. ................................... 606/2; 606/16; 606/17
[58] Field of Search ................................. 606/1, 14, 15, 606/16, 17, 10, 11, 12

[56] References Cited

U.S. PATENT DOCUMENTS

| | | | |
|---|---|---|---|
| 4,657,014 | 4/1987 | Edelman et al. | 606/15 |
| 5,156,604 | 10/1992 | Hessel et al. | 606/15 |
| 5,300,063 | 4/1994 | Tano et al. | 606/15 |
| 5,342,198 | 8/1994 | Vassiliadis et al. | 606/15 |
| 5,342,358 | 8/1994 | Daikuzono | 606/15 |
| 5,395,361 | 3/1995 | Fox et al. | 606/16 |
| 5,416,878 | 5/1995 | Bruce | 606/15 |
| 5,456,603 | 10/1995 | Kowalyk et al. | 606/16 |
| 5,607,420 | 3/1997 | Schuman | 606/17 |
| 5,688,264 | 11/1997 | Ren et al. | 606/15 |
| 5,693,043 | 12/1997 | Kittrell et al. | 606/15 |
| 5,713,894 | 2/1998 | Murphy-Chitorian et al. | 606/17 |
| 5,785,521 | 7/1998 | Riloiu et al. | 606/16 |
| 5,833,684 | 11/1998 | Franetzki | 606/16 |
| 5,849,007 | 12/1998 | Fuhrberg et al. | 606/16 |
| 5,851,112 | 12/1998 | Daikuzon | 606/16 |

*Primary Examiner*—Linda C. M. Dvorak
*Assistant Examiner*—Soya C Harris
*Attorney, Agent, or Firm*—Koda & Androlia

[57] ABSTRACT

A medical laser treatment device comprises a handpiece having a handpiece body and a laser probe to be attached to the handpiece body, a laser light source, and a light transmission member which guides laser light to the handpiece. The laser probe has a fiber probe having an emission face through which the laser light is emitted to an irradiation region, an annular protection tube which covers the peripheral face of the fiber probe, and a holder which holds the fiber probe and the protection tube. The protection tube has a curved part extending with being curved. A first fiber curved part is formed in the fiber probe by passing the fiber probe through the protection tube. A second fiber curved part having a radius of curvature is smaller than that of the first fiber curved part is disposed in a tip end portion of a fiber probe.

12 Claims, 13 Drawing Sheets

ENERGY LEVEL

ENERGY LEVEL

MEDICAL LASER TREATMENT DEVICE AND LASER PROBE FOR THE SAME

BACKGROUND OF THE INVENTION

1. Field of the Invention

The present invention relates to a medical laser treatment device for irradiating a diseased part with laser light to be treated, and a laser probe for such a device. More particularly, the invention relates to a medical laser treatment device useful in fields such as dentistry, dental surgery, and otolaryngology, and a laser probe useful for such a device.

2. Description of the Related Art

Conventionally, laser light is used for treatments such as coagulation, blood stanching, evaporation, and incision on a diseased part, conducting an analgesic action, or for polymerization of a material containing a photopolymerizing agent applied to a diseased part. A medical laser treatment device using laser light comprises a handpiece having a handpiece body to be grasped by an operator, and a laser probe to be attached to a tip end of the handpiece body; a laser light source for generating laser light; a fluid source for supplying a fluid such as water; a light transmission member for guiding the laser light emitted from the laser light source to the handpiece; and a fluid supply passage through which the fluid is supplied from the fluid source to the handpiece body. The laser probe includes a fiber probe. An incidence face is formed at one end of the fiber probe, and an emission face at the other end. Laser light transmitted from the laser light source through the light transmission member impinges on the incidence face of the fiber probe to travel in the fiber probe, and is then emitted from the emission face toward a diseased part. The fluid supplied from the fluid source through the fluid supply passage is sprayed toward the diseased part which is irradiated with the laser light, as required.

When such a medical laser treatment device of the prior art is used in a treatment, particularly in a dental treatment, the action of treatment must be conducted in a mouth while using the fiber probe. In a mouth, the space which is available for such a treatment is extremely restricted. Therefore, there is a problem in that, depending on the position of a diseased part, it becomes very difficult to irradiate the diseased part with laser light.

In order to solve this problem, for example, a handpiece 302 as shown in FIG. 21 is proposed. In the proposed handpiece 302, a part of a fiber probe 304 is curved. When the fiber probe 304 having such a curved part is used, the fiber probe can be easily inserted into a narrower space as compared with a case of the prior art, such as a gap formed between adjacent teeth.

Therefore, the treatment range is widened particularly in the field of dentistry.

However, the fiber probe 304 having such a curved part is not satisfactorily used in the field of dentistry or the like.

When a diseased part is in the branched root bottom, root surface and occlusal surface of a molar, in adjacent surfaces of adjacent teeth, or on the distal side surface and cheek side surface of a periodontal pocket or a molar, for example, the diseased part can not be irradiated with laser light from the front of the emission face of the fiber probe, thereby producing a problem that the laser treatment cannot be performed in a sufficiently effective manner.

Furthermore, there is another problem that, when laser irradiation is performed by using the fiber probe 304 having the curved part, the position of the curved part or the degree of the radius of curvature of the curved part may cause a problem that laser light having nonuniform energy is emitted from the emission face of the fiber probe 304.

SUMMARY OF THE INVENTION

It is an object of the invention to provide a medical laser treatment device which can easily perform a laser treatment even in a relatively small body cavity such as an oral cavity, a nasal cavity, an ear cavity, or a throat, and to provide a laser probe which is used for the same.

It is another object of the invention to provide a medical laser treatment device in which the energy of laser light emitted from an emission face of a fiber probe is uniformized, thereby enhancing the durability of the fiber probe, and a laser probe for use in the device.

In a first aspect of the invention, there is provided a medical laser treatment device comprising: a handpiece having a handpiece body and a laser probe to be attached to a tip end of the handpiece body; a laser light source for generating laser light; a fluid source for supplying a fluid; a light transmission member for guiding the laser light emitted from the laser light source to the handpiece; and a fluid supply passage through which the fluid is supplied from the fluid source to the handpiece body, wherein the laser probe includes a fiber probe having an emission face through which the laser light from the light transmission member is emitted to an irradiation region, an annular protection tube for covering a peripheral face of the fiber probe, and a holder for holding the fiber probe and the protection tube, which holder is attached to the tip end of the handpiece body, wherein between the fiber probe of the laser probe and the protection tube is defined an annular fluid passage space, through which the fluid supplied through the fluid supply passage is sprayed, wherein the protection tube has a curved part which bends and extends with respect to an axis of the handpiece body, and the fiber probe has a first fiber curved part extending along the curved part which is formed by inserting the fiber probe into the protection tube to pass therethrough, wherein a tip end portion of the fiber probe projects outwardly from a tip end of the protection tube, which tip end portion has a second fiber curved part disposed in the projecting tip end portion so that the emission face is directed laterally with respect to an axial direction of the tip end portion, and wherein a radius of curvature (R1) of the first fiber curved part is greater than a radius of curvature (R2) of the second fiber curved part (R1>R2).

According to the first aspect of the invention, since the fiber probe has the first fiber curved part and the second fiber curved part which is disposed in the tip end portion of the fiber probe, laser irradiation can be easily performed while moving the emission face of the fiber probe, even in a relatively small body cavity such as an oral cavity or ear cavity. Since the radius of curvature of the first fiber curved part is greater than that of the second fiber curved part, the tip end portion of the fiber probe can be easily located at a position such as that below a molar, in the proximal surface of adjacent teeth, or on the distal side of a periodontal pocket.

Since the first fiber curved part of the fiber probe is formed by inserting the fiber probe into the curved protection tube, the first fiber curved part can be easily formed without requiring a special production step for forming the first fiber curved part. Since the annular fluid passage space is formed between the fiber probe and the protection tube, the fluid from the fluid source can pass through the fluid passage space to be sprayed toward the laser irradiation region.

In a second aspect of the invention, the first fiber curved part of the fiber probe is curved by 30° to 90° and extends with respect to the axis of the handpiece body, and the second fiber curved part of the fiber probe is curved in any one of a direction substantially identical with the curved direction of the first fiber curved part, a direction substantially opposite to the curved direction, and a direction substantially perpendicular to the directions.

According to the second aspect of the invention, since the first fiber curved part of the fiber probe is curved by 30° to 90° with respect to the axis of the handpiece body and the second fiber curved part is disposed in the tip end portion of the fiber probe, the tip end portion can be easily located at a position such as that below a molar, in the proximal surface of adjacent teeth, or on the distal side of a periodontal pocket.

In a third aspect of the invention, the second fiber curved part of the fiber probe is formed by curving the tip end portion of the fiber probe in a heated state so that the emission face is laterally directed.

According to the third aspect of the invention, since the second fiber curved part of the fiber probe is formed by curving the tip end portion in a heated state, so that the emission face is laterally directed, the second fiber curved part can be formed in a relatively easy manner.

In a fourth aspect of the invention, the radius of curvature (R2) of the second fiber curved part of the fiber probe is not smaller than a diameter (D) of the fiber probe and not larger than five times (5D) the diameter of the fiber probe (5D≧R2≧D).

According to the fourth aspect of the invention, since the radius of curvature of the second fiber curved part is not smaller than the diameter of the fiber probe and not larger than five times the diameter, light propagating through the fiber probe is prevented from exceeding a critical angle or from leaking to an outside of the fiber probe.

In a fifth aspect of the invention, the fiber probe is constituted by a multifiber composed of a plurality of optical fibers each having a core and a clad which covers the core.

According to the fifth aspect of the invention, since the fiber probe is constituted by a multifiber, the energy of the laser light emitted from the fiber probe can be uniformized. Laser light incident on each of the optical fibers constituting the multifiber is transmitted to the emission end as it is. When light uniformly enters the incidence face, therefore, uniformized light is emitted from the emission face.

In a sixth aspect of the invention, laser light generated by the laser light source has a wavelength of 1.0 to 5.5 μm and the fiber probe has a diameter of 0.2 to 3.0 mm.

According to the sixth aspect of the invention, the device can be beneficially used for laser treatment in a relatively small body cavity such as the oral cavity or the ear cavity.

In a seventh aspect of the invention, a laser probe for medical laser treatment devices comprises a fiber probe for receiving laser light from a handpiece body through an incidence face formed at one end of the fiber probe and emitting the laser light from an emission face formed at another end of the fiber probe, toward an irradiation region, wherein the fiber probe has a fiber curved part at the another end portion so that the emission face is laterally directed with respect to an axis of the fiber probe, the emission face extends substantially in parallel with the axis of the fiber probe, a radius of curvature of the fiber curved part is within a range of 0.5 mm to 3.0 mm, and the emission face projects from a peripheral face of the fiber probe by 0 to 3.0 mm.

According to the seventh aspect of the invention, since the radius of curvature of the fiber curved part of the fiber probe is within a range of 0.5 to 3.0 mm, the emission face extends substantially in parallel with the axis of the fiber probe, and the emission face projects from the peripheral face of the fiber probe by 0 to 3.0 mm, a treatment can be easily performed while the position of the emission face of the fiber probe is changed, in a relatively small body cavity such as the oral cavity or the ear cavity.

In an eighth aspect of the invention, a laser probe for medical laser treatment devices comprises a fiber probe for receiving laser light from a handpiece body through an incidence face formed at one end of the fiber probe and emitting the laser light from an emission face formed at another end of the fiber probe, toward an irradiation region, wherein the fiber probe linearly extends in an axial direction of the fiber probe in a range from the one end to a vicinity of a center portion of the fiber probe, and has a fiber curved part in a region from the vicinity of the center portion to the other end, and a tapered portion in which the emission face extends in the axial direction in a linearly inclined manner is formed in the another end portion of the fiber probe.

According to this configuration, since the fiber probe linearly extends in a range from the one end to a vicinity of the center portion, the fiber curved part is disposed in a region from a vicinity of the center portion to the other end, and the tapered portion is formed in the other end portion of the fiber probe, laser light is laterally emitted in the other end portion, with the result that the laser probe can be beneficially used in the field of dentistry.

In a ninth aspect of the invention, a laser probe for a medical laser treatment device comprises a fiber probe for receiving laser light from a handpiece body through an incidence face formed at one end of the fiber probe and emitting the laser light from an emission face formed at another end of the fiber probe, toward an irradiation region, wherein the fiber probe linearly extends in an axial direction of the fiber probe in a range from the one end to a vicinity of a center portion of the fiber probe, and has a first fiber curved part in a region from the vicinity of the center portion to the other end, and a second fiber curved part at the another end portion of the fiber probe so that the emission face is laterally directed with respect to an axis of the other end portion, and a radius of curvature (R1) of the first fiber curved part is greater than a radius of curvature (R2) of the second fiber curved part (R1>R2).

According to the ninth aspect of the invention, since the fiber probe linearly extends in a range from the one end to a vicinity of the center portion, the first fiber curved part is disposed in a region from a vicinity of the center portion to the other end, and the second fiber curved part is disposed in the tip end portion, laser irradiation can be easily performed while changing the position of the emission face of the fiber probe, even in a relatively small body cavity such as the oral cavity or the ear cavity. Since the radius of curvature of the first fiber curved part is greater than that of the second fiber curved part, a treatment can be performed while the tip end portion of the fiber probe is easily located at a position such as that below a molar, in the proximal surface of adjacent teeth, or on the distal side of a periodontal pocket.

In a tenth aspect of the invention, the second fiber curved part of the fiber probe is curved in one of a direction which is substantially identical with the curved direction of the first fiber curved part, a direction which is substantially opposite to the curved direction, and a direction which is substantially perpendicular to the directions.

According to the tenth aspect of the invention, since the second fiber curved part is curved as required, the other end can be easily located at a position such as that below a molar, in the proximal surfaces of adjacent teeth, or on the distal side of a periodontal pocket.

In an eleventh aspect of the invention, the fiber probe is configured by a multifiber composed of a plurality of optical fibers each having a core and a clad which covers the core.

According to the eleventh aspect of the invention, since the fiber probe is constituted by a multifiber, the energy of the laser light emitted from the emission face can be uniformized.

In a twelfth aspect of the invention, the emission face of the fiber probe has one of a conical face, a tapered face, a semispherical face, and a flat face which extends in the axial direction.

According to the twelfth aspect of the invention, since the emission face of the fiber probe has one of the above-mentioned faces, the laser probe can be beneficially used in the field of dentistry.

BRIEF DESCRIPTION OF THE DRAWINGS

Other and further objects, features, and advantages of the invention will be more explicit from the following detailed description taken with reference to the drawings wherein.

DETAILED DESCRIPTION OF THE PREFERRED EMBODIMENTS

Figure 1:
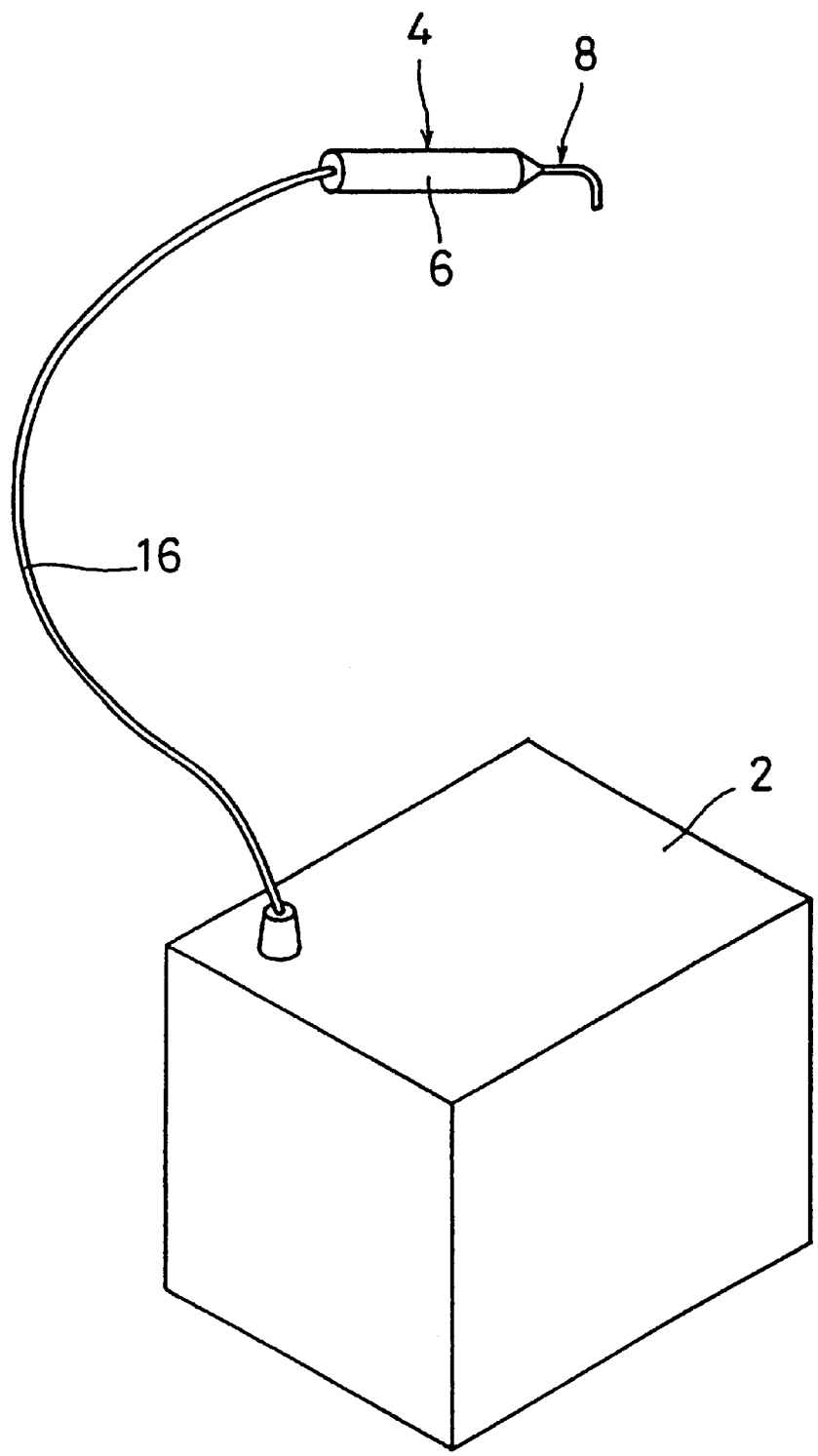
FIG. 1 is a perspective view showing the whole of an embodiment of a medical laser treatment device of the invention.

Now referring to the drawings, preferred embodiments of the invention are described below.

Figure 2:
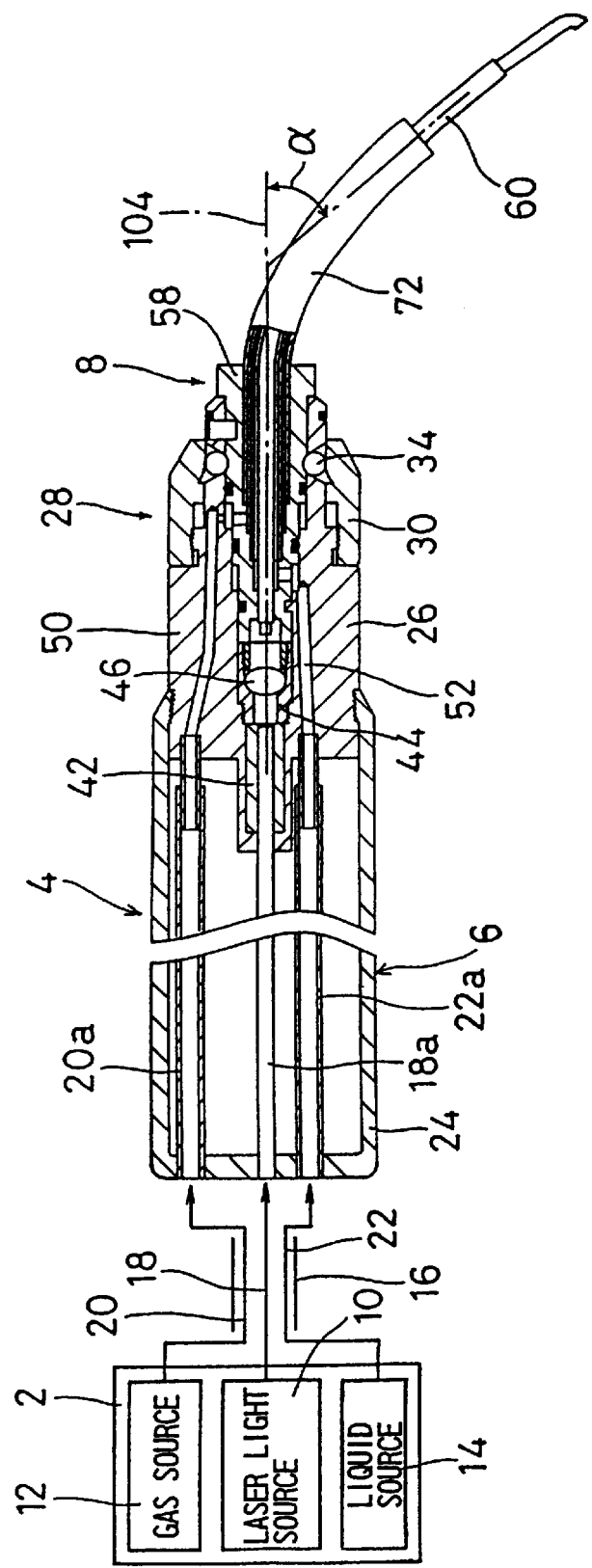
FIG. 2 is a section view of a handpiece of the medical laser treatment device of FIG. 1.

FIG. 1 is a perspective view showing the whole of an embodiment of a medical laser treatment device of the invention, and FIG. 2 is a section view of a handpiece of the medical laser treatment device of FIG. 1.

Referring to FIGS. 1 and 2, the illustrated medical laser treatment device comprises the body 2 of the medical laser treatment device, and a laser handpiece 4. The laser handpiece 4 has the handpiece body 6 which is to be grasped by the operator, and a laser probe 8 which is detachably attached to the tip end of the handpiece body 6.

The medical laser treatment device body 2 incorporates a laser light source 10 which generates laser light, a gas source 12 which supplies a gas such as air or an inert gas, and a liquid source 14 which supplies a liquid such as water or physiological saline. The laser light from the laser light source 10, the gas from the gas source 12, and the liquid from the liquid source 14 are supplied to the handpiece 4 through a medium supply cable 16. The medium supply cable 16 incorporates a light transmission member 18 consisting of, for example, an optical fiber, a gas supply pipe 20 which forms a gas supply passage, and a liquid supply pipe 22 which forms a liquid supply passage.

One end of the light transmission member 18 is connected to the laser light source 10, and the other end portion 18a extends into the handpiece body 6. One end of the gas supply pipe 20 is connected to the gas source 12, and the other end portion 20a extends into the handpiece body 6. One end of the liquid supply pipe 22 is connected to the liquid source 14, and the other end portion 22a extends into the handpiece body 6.

Figure 3:
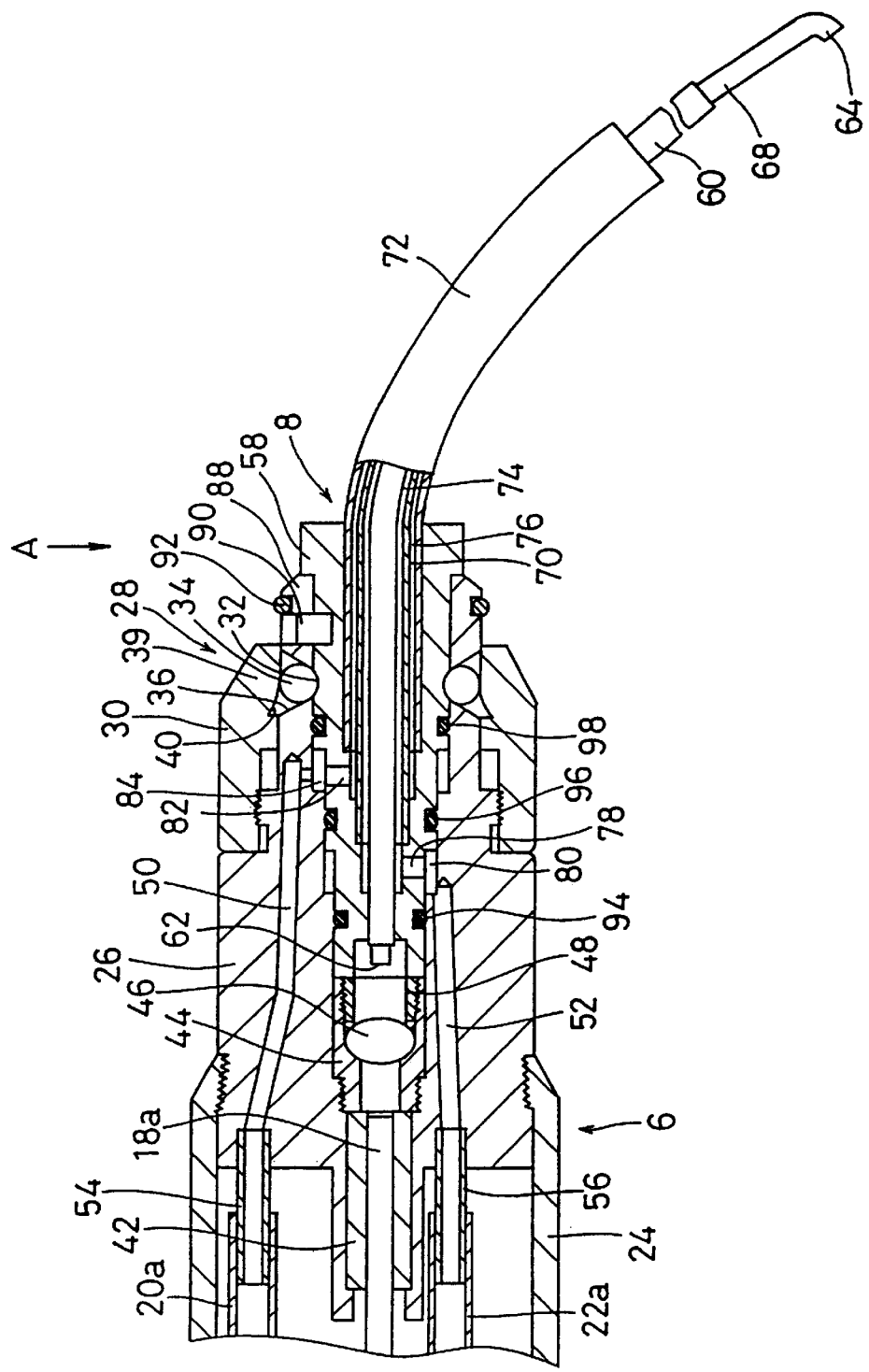
FIG. 3 is a partial enlarged section view showing a tip end portion of the handpiece of FIG. 2 in an enlarged manner.

Referring to FIG. 3 together with FIG. 2, the handpiece body 6 has a cylindrical hollow handpiece housing 24, and the other end portions 18a, 20a, and 22a of the light transmission member 18, the gas supply pipe 20, and the liquid supply pipe 22 extend in the handpiece housing 24 in the axial direction toward the tip end side (the right side in FIGS. 2 and 3). A cylindrical intermediate member 26 is attached to the tip end portion of the handpiece housing 24, and the laser probe 8 is attached to the intermediate member 26. A female thread is formed in the inner peripheral face of the tip end portion of the housing 24, and a male thread is formed in the outer peripheral face of the rear end portion of the intermediate member 26. The intermediate member 26 is attached to the housing 24 by coupling the female and male threads with each other.

At tip end portion of the intermediate member 26 is arranged an attaching mechanism 28 for detachably attaching the laser probe 8. The attaching mechanism 28 comprises a cover nut 30 which is to be attached to the tip end portion of the intermediate member 26. A male thread is formed in the tip end portion of the intermediate member 26, and a female thread is formed in the rear end portion of the cover nut 30. The cover nut 30 is attached to the intermediate member 26 by coupling the female and male threads with each other. The attaching mechanism 28 further comprises a plurality of ball members 34 which are engageable with an annular recess 32 (see also FIG. 5) formed in a part of the laser probe 8. The ball members 34 are housed in an annular housing groove 36 formed in the tip end portion of the intermediate member 26. A pressing portion 39 which presses the ball members 34 toward the inside in a radial direction, and an inclined portion 40 which is used for canceling the pressurization exerted on the ball members 34 and which has an increased inner diameter are disposed in the tip end portion of the cover nut 30. According to this configuration, when the cover nut 30 is tightened, the pressing portion 39 presses the ball members 34 toward the inside in a radial direction. This causes the ball members 34 to engage with the annular recess 32 formed in the outer periphery of a holder 58. In this way, the laser probe 8a is detachably attached to the intermediate member 26 of the handpiece body 6. By contrast, when the cover nut 30 is loosened, the inclined portion 40 of the nut is located at a position which is more outward than the ball members 34 bin a radial direction, thereby canceling the pressurization exerted on the ball members 34 by the pressing portion 39. In this state, when the laser probe h is pulled toward the tip end side, the laser probe can be detached from the handpiece body 6.

The intermediate member 26 is configured in the following manner. In the embodiment, a ferrule 42 is attached to the rear end portion of the intermediate member 26. The other end portion 18a of the light transmission member 18 is supported by the ferrule 42. In the intermediate member 26, a lens holder 44 is attached to a tip potion of the ferrule 42 in the tip end direction of the laser handpiece 4. The lens holder 44 is attached to the intermediate member 26 by screw fastening the female thread of the intermediate member 26 with the male thread of the lens holder 44. A lens 46 is disposed in the lens holder 44, and attached to the lens holder 44 by screw fastening the female thread of the lens holder 44 with the male thread of a fixing sleeve 48. The lens 46 may be fixed to the lens holder 44, for example, by an adhesive in lieu of the fixing sleeve 48. The lens 46 is disposed so as to be opposed to the other end face of the light transmission member 18, and collects the laser light from the light transmission member 18 to guide the laser light to the laser probe 8.

A gas passage 50 and a liquid passage 52 are formed in the intermediate member 26. The gas passage 50 and the liquid passage 52 extend in the axial direction of the handpiece body 6 (the lateral direction in FIGS. 2 and 3). A connection pipe 54 is fixed to an one end of the gas passage 50, and the other end 20a of the gas supply pipe 20 is connected to the connection pipe 54. A connection pipe 56 is fixed to an one end of the liquid passage 52, and the other end 22a of the liquid supply pipe 22 is connected to the connection pipe 56. According to this configuration, the gas from the gas source 12 is supplied to the gas passage 50 through the gas supply pipe 20, and the liquid from the liquid source 14 is supplied to the liquid passage 52 through the liquid supply pipe 22.

The laser probe 8 will be described with reference to mainly FIG. 5 together with FIG. 3. The illustrated laser probe 8 has the holder 58 which is attached to the tip end portion of the intermediate member 26 by the cover nut 30, and a fiber probe 60 which is attached to the holder 58. The holder 58 has a slim shape, and one end portion (rear end portion) of the holder is inserted into the tip end portion of the intermediate member 26. The fiber probe 60 is attached to the center portion of the holder 58 with passing therethrough. An incidence face 62 of the one end is exposed in one end face of the holder 58 and positioned so as to be opposed to the lens 46. The other end portion, i.e., the tip end portion of the fiber probe 60 extends further outward from the end face of the holder 58. An emission face 64 is disposed in the other end of the fiber probe 60. Laser light entering through the incidence face 62 is emitted from the emission face 64 toward an irradiation region of a diseased part through the fiber probe 60. The fiber probe 60 has a core (not shown) which exists at the center, and a clad 66 which covers the core. The clad 66 is covered by a protection jacket 68.

Figure 5:
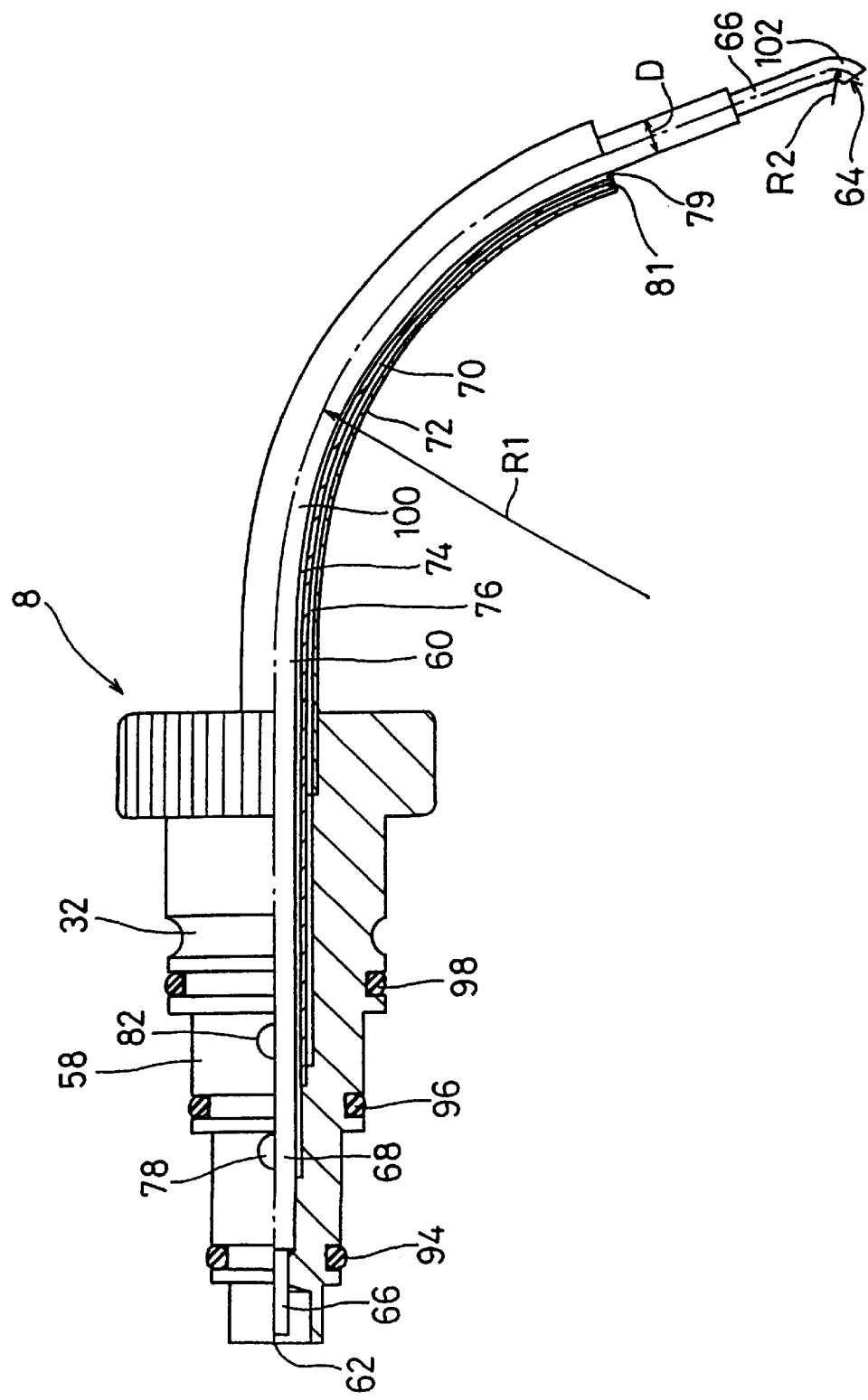
FIG. 5 is a half section view of a laser probe of the handpiece of FIG. 2, showing the lower side in section.

In the embodiment, as shown in FIG. 5, the protection jacket 68 is peeled off in both the ends of the fiber probe 60 so that the inner clad 66 is exposed to the outside.

A first pipe 70 and a second pipe 72 which are hollowed (both the pipes constitute a protection tube) are attached to the holder 58 of the laser probe 8. The first pipe 70 is disposed so as to cover the fiber probe 60. One end of the pipe extends to a vicinity of the one end portion of the fiber probe 60 and the other end to a vicinity of the other end portion of the fiber probe 60. The second pipe 72 is disposed so as to cover the first pipe 70. One end of the pipe extends to a vicinity of one end portion of the first pipe 70 and the other end to a vicinity of the other end portion of the first pipe 70. The first and second pipes 70 and 72 are made of, for example, stainless steel. As shown in FIG. 5, the first pipe 70 is placed so as to be substantially concentrical with the fiber probe 60, and an annular first fluid passage space 74 is defined between the first pipe 70 and the fiber prove 60. The second pipe 72 is placed so as to be substantially concentrical with the first pipe 70, and an annular second fluid passage space 76 is defined between the first pipe 70 and the second pipe 72. As shown in FIG. 5, the other end portion of the fiber probe 60 projects from the first and second pipes 70 and 72, and the protection jacket 68 is peeled off in a range from an intermediate position of the project end portion and the other end (the tip end).

One end of the first fluid passage space 74 extends to a vicinity of one end of the holder 58. A supply hole 78 which communicates with the one end portion of the first fluid passage space 74 is formed in the holder 58. An annular space 80 is formed between the intermediate member 26 and the holder 58.

The supply hole 78 communicates with the annular space 80 which communicates with the liquid passage 52. According to this configuration, the liquid supplied through the liquid supply pipe 22 is supplied to the first passage space 74 through the liquid passage 52, the annular space 80, and the supply hole 78, and then sprayed from an opening 79 formed in the other end (tip end) of the passage space 74. One end of the second fluid passage space 76 extends to a vicinity of a center portion in the axial direction of the holder 58. A supply hole 82 which communicates with the one end portion of the second passage space 76 is formed in the holder 58. An annular space 84 also is formed between the intermediate member 26 and the holder 58. The supply hole 82 communicates with the annular space 84 which communicates with the gas passage 50. According to this configuration, the gas supplied through the gas supply pipe 20 is supplied to the second fluid passage space 76 through the gas passage 50, the annular space 84, and the supply hole 82, and then sprayed from an opening 81 formed in the other end (tip end) of the passage space 76. The liquid supply through the first passage space 74, and the gas supply through the second passage space 76 may be suitably selected in accordance with the contents of a treatment using the medical laser treatment device. Either of the supply of the gas only, that of the liquid only, and that of a mixture of the gas and the liquid (in this case, mist-like liquid is obtained) can be performed toward the irradiation range of laser light.

Figure 4:
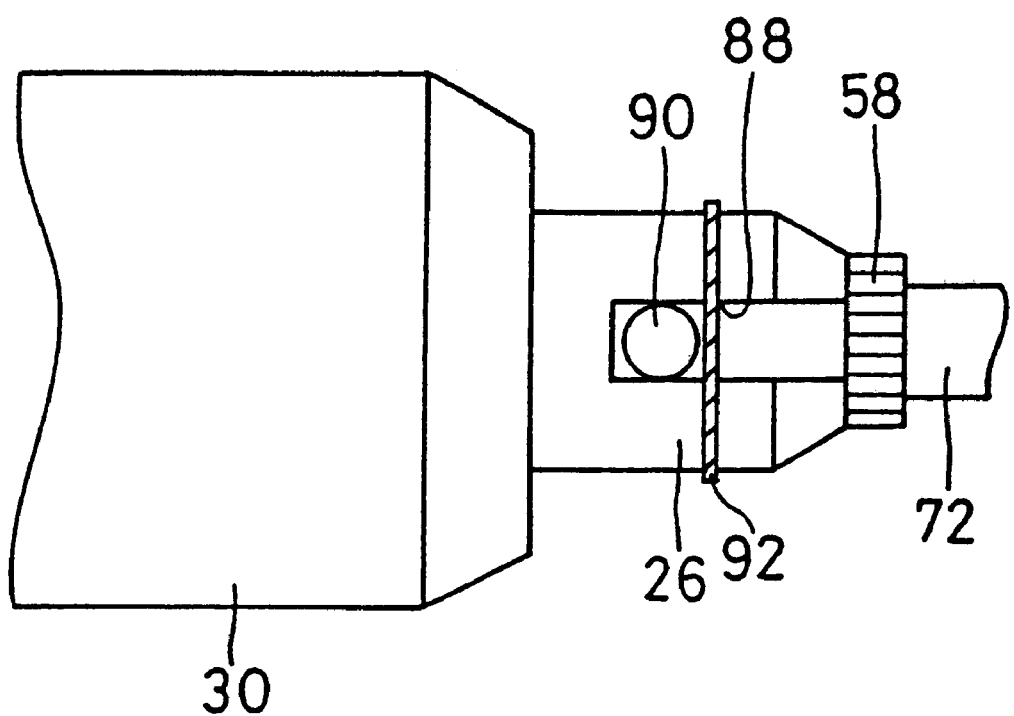
FIG. 4 is a partial enlarged section view as seen in a direction of an arrow A in FIG. 3.

In the embodiment, the holder 58 is prevented from being relatively rotated with respect to the intermediate member 26, in the following manner. Referring to FIGS. 3 and 4, a recess 88 which extends in the axial direction from the other end (tip end) of the intermediate member 26 and toward one end is formed at a predetermined position of the intermediate member. A pin 90 is fixed to the holder 58 so as to correspond to the recess 88. When the laser probe 8 is to be attached, the pin 90 is positioned in the recess 88 of the intermediate member 26, and the holder 58 is inserted into the intermediate member 26 in the state where this positioning is performed. In order to prevent the cover nut 30 in a loose state from slipping off, a lock ring 92 is engaged with the tip end portion of the intermediate member 26. The disposition of the pin 90 surely prevents the laser probe 8 from being relatively rotated with respect to the intermediate member 26. As a result, a detachable configuration in which the angle of the fiber probe 60 is not changed during a treatment and such a relative rotation is prevented from occurring can attained. In order to prevent the gas and liquid from leaking, O-rings 94, 96, and 98 are disposed between the intermediate member 26 and the holder 58 so as to respectively correspond to the supply holes 78 and 82.

When the medical laser treatment device is to be used in a field such as dentistry, dental surgery, or otolaryngology, it is preferable to use laser light of a wavelength of 0.5 to 5.5 μm. As such a laser device, useful is a solid-state laser such as Er:YAG (Erbium-Yttrium-Aluminum-Garnet), Er:YSGG (Erbium-Yttrium-Scandium-Gallium-Garnet), Ho:YAG (Holmium-Yttrium-Aluminum-Garnet), Th:YAG (Thorium-Yttrium-Aluminum-Garnet), Co:VF (Cobalt-Vanadium-Fluoride), Er:GLASS (Erbium-GLASS), Nd:GLASS (Neodymium-GLASS), Nd:YAG (Neodymium-Yttrium-Aluminum-Garnet), or Ti:Sa (Titanium-Sapphire), or a gas laser such as CO (carbon dioxide) laser.

In the above-mentioned fields, when the medical laser treatment device is to be used in a relatively small body cavity such as the oral cavity, the nasal cavity, the ear cavity, or the throat, it is preferable to use a laser probe in which the fiber probe 60 has a diameter of 0.2 to 3.0 mm.

In the case where such a medical laser treatment device is to be used in the filed of dentistry, for example, the shape of the fiber probe 60, which may depend on the kind of a treatment, is preferably set in the following manner. Referring to mainly FIG. 5, the illustrated fiber probe 60 has a first fiber curved part 100 and a second fiber curved part 102 as shown in FIG. 5. In the illustrated embodiment, the fiber probe 60 in a range from the one end to a vicinity of the center portion (approximately a half) in the axial direction of the fiber probe extends substantially in parallel with the axis 104 of the handpiece body 6 (as shown in FIG. 2, the axis of this portion substantially coincides with the axis 104). The first fiber curved part 100 is continuous to the above-mentioned linear portion. The first fiber curved part 100 extends with being curved by about 45° with respect to the axis 104 of the handpiece body 6. In other words, the angle a (FIG. 2) of the portion which linearly extends in the one end portion and the other end portion of the fiber probe 60 is set to be about 45°. The angle α varies depending on the kind of a tooth to be treated and the position of the tooth. In the case of a dental treatment, when the angle is set to be in the range of 30 to 90°, laser light irradiation can be easily performed at various positions. This angle is related also to the second fiber curved part 102 which will be described later.

The first fiber curved part 100 is formed in the following manner. A predetermined portion of each of the first and second pipes 70 and 72 which are made of a metal such as stainless steel is curved into a shape which corresponds to a radius of curvature R1 (FIG. 5). By contrast, in the fiber probe 60, the portion corresponding to the first fiber curved part 100 is linearly formed. When the fiber probe 60 is inserted into the first pipe 70 during a process of assembling the fiber probe 8, the portion of the fiber probe 60 which portion corresponds to the curved portion of the first pipe 70 is forcedly curved along the curved portion because the fiber probe 60 is flexible. In this way, the first fiber curved part 100 is formed. Therefore, the first fiber curved part 100 can be easily formed only by inserting the fiber probe 60 into the first pipe 70.

The second fiber curved part 102 is disposed in the other end portion (tip end portion) of the fiber probe 60. The other end portion of the fiber probe 60 linearly extends from the first fiber curved part 100, and the second fiber curved part 102 is disposed in the other end portion which linearly extends, and the other end portion and the second fiber curved part 102 are stripped of the protection jacket 68. The radius of curvature R2 (FIG. 5) of the second fiber curved part 102 (the radius of curvature of the center axis of the second fiber curved part 102) is set to be smaller than the radius of curvature R1 of the first fiber curved part 100 (the radius of curvature of the center axis of the first fiber curved part 100) (R1>R2). In the configuration wherein the radius of curvature R2 of the second fiber curved part 102 is made smaller in this way, the emission face of the tip end portion of the fiber probe 60 can be easily located in front of a diseased part at a position such as that below a molar, in the proximal surface of adjacent teeth, or on the distal side of a periodontal pocket.

Preferably, the radius of curvature R2 of the second fiber curved part 102 is set to have a value which is not smaller than the diameter D (FIG. 5) of the fiber probe 60 (R2≧D) and not larger than five times the diameter (5D) of the fiber probe 60 (5D≧R2). As a result of this setting, light emitted from the emission face 64 can be compactly guided to the front of the objective diseased part.

For example, the second fiber curved part 102 is formed in the following manner. The tip end portion of the fiber probe 60 is heated to about 1,600° C. to be softened. In the softened state, the tip end portion is curved by using a curving tool (not shown) so that the emission face 64 is laterally directed with respect to the axis which linearly extends in the tip end portion or, in the embodiment, curved in the same direction as the curved direction of the first fiber curved part 100. When the curving operation is performed while heating and softening in this way, the second fiber curved part 102 of a small radius of curvature can be formed without being damaged.

Figure 6:
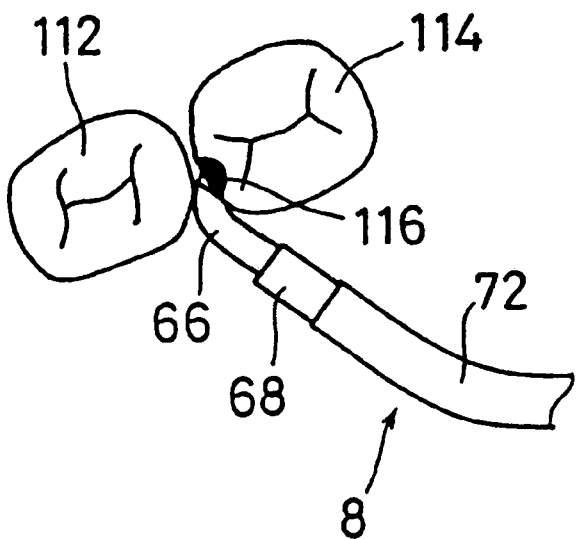
FIG. 6 is a schematic view showing an example of treatment using the laser probe of FIG. 4.

The fiber probe 60 having the thus configured first and second fiber curved parts 100 and 102 can be beneficially used in, particularly, a dental treatment. As shown in FIG. 6, for example, the emission face 64 of the tip end of the fiber probe 60 can be easily positioned in a gap between adjacent molars 112 and 114. Therefore, the emission face 64 can be opposed to the front of caries 116 which is in the proximal surface of the molar 114, with the result that the caries 116 in the proximal surface of the molar 114 can be effectively irradiated with laser light.

Figure 7:
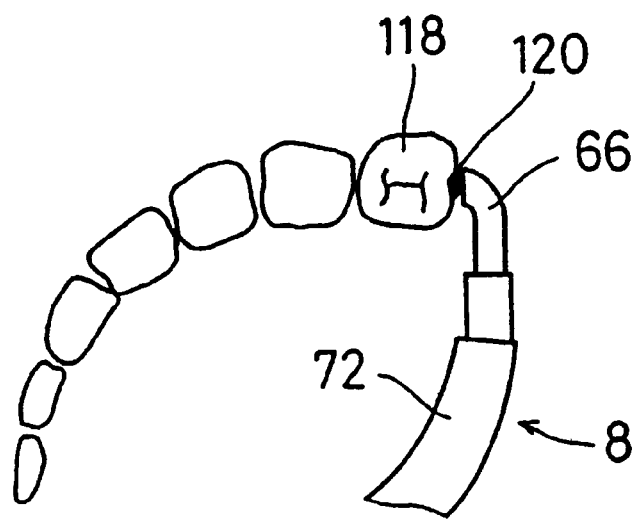
FIG. 7 is a schematic view showing another example of treatment using the laser probe of FIG. 4.

As shown in FIG. 7, for example, the emission face 64 of the tip end of the fiber probe 60 can be easily positioned on the distal side of a molar 118, from the front side. Therefore, the emission face 64 can be opposed to the front of caries 120 which is in the distal side of the molar 118, with the result that the caries 120 in the distal side of the molar 118 can be effectively irradiated with laser light.

Figure 8A:
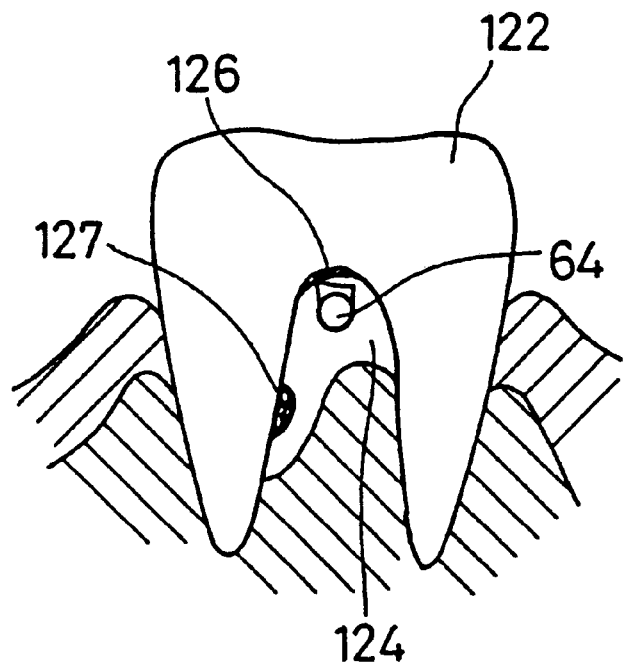
FIGS. 8A and 8B are schematic section views respectively showing further examples of treatment using the laser probe of FIG. 5.
Figure 8B:
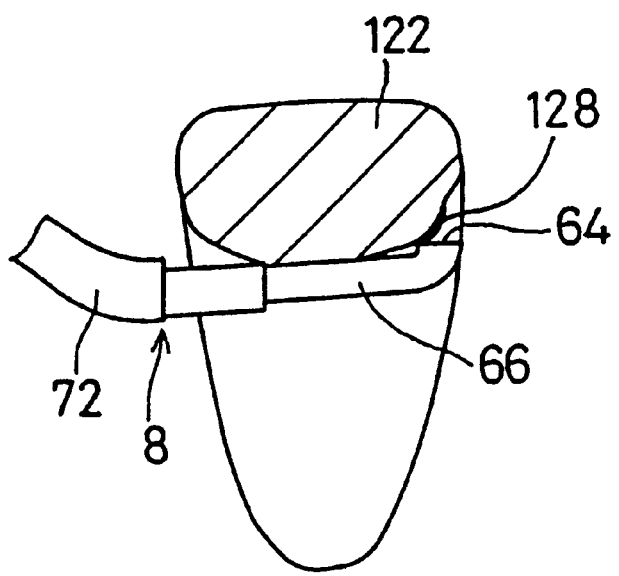

As shown in FIGS. 8A and 8B, for example, the tip end portion of the fiber probe 60 can be easily inserted into calculus on a molar root bifurcation 122 and a periodontal pocket 124.

Thereby, the emission face 64 of the fiber probe 60 can be opposed to the front of calculi 126 and 127 (see FIG. 8A) which are on the bottom and inner side faces of the root bifurcation of a molar 122, and also calculus 128 which is on the side face of the root bifurcation, and the laser probe is applicable to removing a calies of a branched root. Consequently the laser light irradiation can be effectively performed toward calculi 126, 127, and 128 which are on the bottom face and the like of the root bifurcation of the molar 122. In the prior art, it is difficult to perform the laser light irradiation on such a face.

Figures 9A, 9B, 9C:
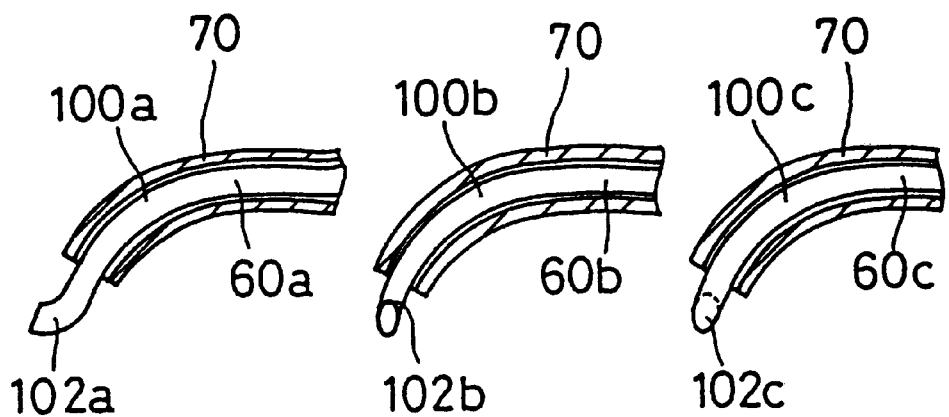
FIGS. 9A, 9B, and 9C are section views schematically showing other embodiments of the fiber probe.

In the fiber probe 60 of the illustrated embodiment, the second fiber curved part 102 is curved in a substantially same direction as the curved direction of the first fiber probe 100. Alternatively, the fiber probes may be formed in another manner as shown in FIGS. 9A to 9C. In a fiber probe 60*a* shown in FIG. 9A, a second fiber curved part 102*a* is curved in a direction, i.e., in an upward direction in FIG. 9A which is opposite to a curved direction of a first fiber curved part 100*a*, i.e., to a downward direction in FIG. 9A. In a fiber probe 60*b* shown in FIG. 9B, a second fiber curved part 102*b* is curved in one lateral direction, i.e., in an approaching direction perpendicular to a sheet in FIG. 9B which is substantially perpendicular to a curved direction of a first fiber curved part 100*b*, i.e., to a downward direction in FIG. 9B. In a fiber probe 60*c* shown in FIG. 9C, a second fiber curved part 102*c* is curved in an other lateral direction, i.e., in a departing direction perpendicular to a sheet in FIG. 9C which is substantially perpendicular to a curved direction of a first fiber probe 100*c*, i.e., to a downward direction in FIG. 9C. The fiber probes 60*a*, 60*b*, and 60*c* shown in FIGS. 9A to 9C may be used in place of the fiber probe 60 shown in FIGS. 1 to 5, or in combination with the fiber probe. When the fiber probes are combinedly used, the above-mentioned treatment is further facilitated.

Figure 10:
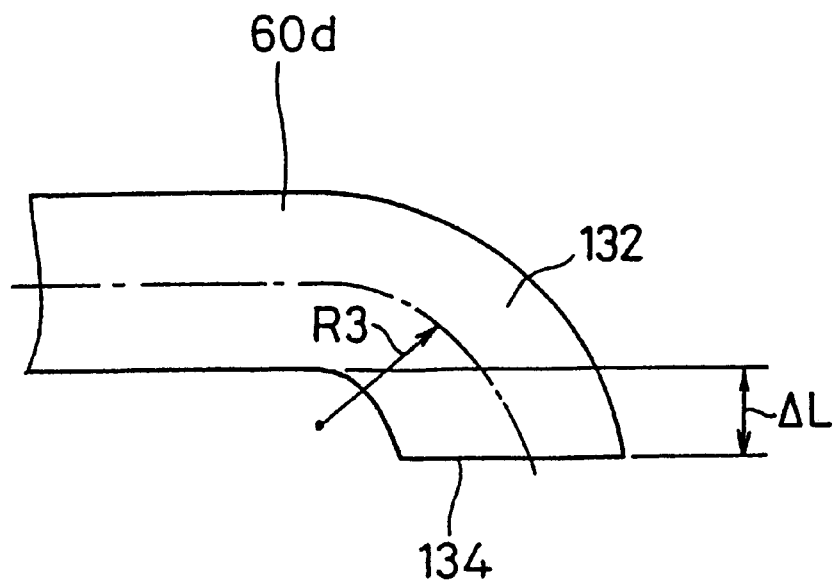
FIG. 10 is a partial enlarged section view showing a further embodiment of the fiber probe.

The emission face of the fiber probe may be formed as shown in FIG. 10. Referring to FIG. 10, in a fiber probe 60*d*, a fiber curved part 132 is disposed in the tip end portion so that the emission face 134 is forward directed. Preferably, the radius of curvature R3 of the fiber curved part 132 of the fiber probe 60*d* is set to be 0.3 to 3.0 mm because of the above-mentioned reason. In the embodiment, the emission face 134 of the tip end of the fiber probe 60*d* extends substantially in parallel with the axis of the fiber probe 60*d* which linearly extends, and the amount of projection ΔL of the emission face 134 from the peripheral face of the fiber probe 60*d* is set to be about 2.0 mm. The emission face 134 having this shape may be applied to a laser probe in which the whole of the fiber probe 60*d* extends in the axial direction in a substantially liner manner, or that in which an intermediate portion of the fiber probe 60*d* has a fiber curved part of a relatively large radius of curvature.

In the fiber probe 60*d* having the emission face 134 of the shape shown in FIG. 10, for example, the emission face 134 can be easily moved along the side face of a molar, and caries or the like adhering to such a portion can be easily irradiated with laser light.

When the amount of projection AL of the emission face 134 is increased, it is difficult to insert the tip end of the fiber probe 60*d* into a narrow gap. Therefore, it is preferable to set the amount of projection ΔL to be 0 to 3.0 mm.

Figure 11:
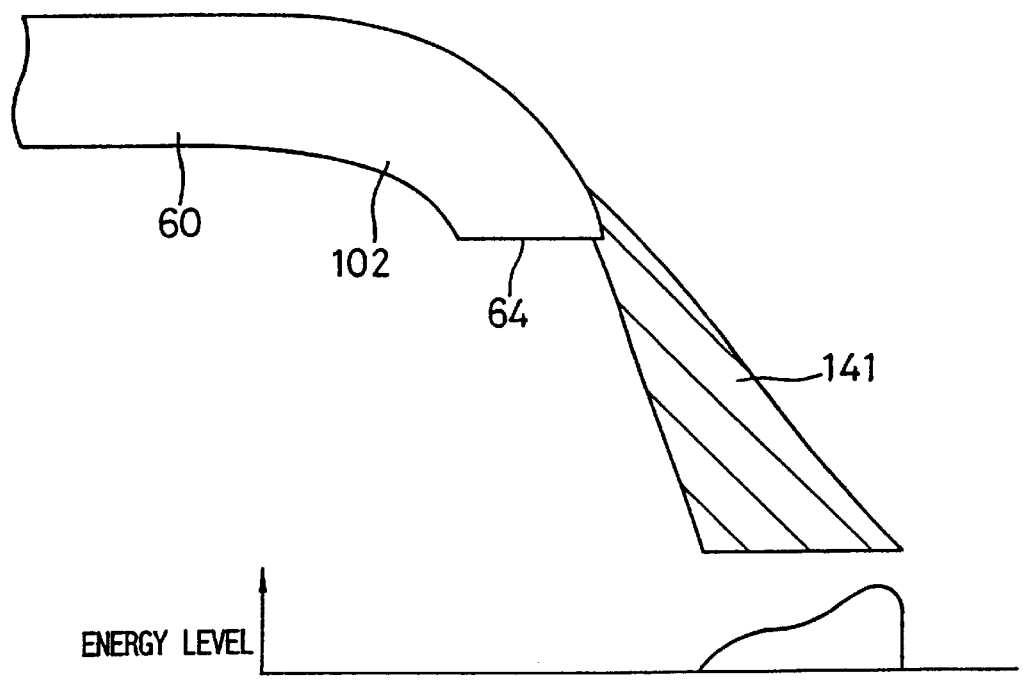
FIG. 11 is a view showing the emission pattern of a fiber probe consisting of a single optical fiber and a distribution of emission energy.

A fiber probe may be configured by, in place of a single optical fiber, a multifiber composed of a plurality of optical fibers. For example, in the case where the fiber probe 60 shown in FIGS. 1 to 5 is configured by a single optical fiber, since the second fiber curved part 102 (having a small radius of curvature) is disposed in the tip end portion, an irradiation light region 141 of laser light emitted from the emission face 64 is as indicated by the hatched portion in FIG. 11, and laser light is concentrated into a portion of a large radius of curvature because the laser light is reflected on the emission face 64. Therefore, laser light emitted from the emission face 64 has the energy distribution shown in the graph of FIG. 11.

Namely, in a portion of a small radius of curvature, the emitted energy is low in level, and, in a portion of a large radius of curvature, the emitted energy is high in level. When the emission energy becomes nonuniform in this way, a diseased part cannot be uniformly irradiated with laser light, and hence a desired treatment cannot be performed. When such an extremely nonuniform state of the energy once occurs, an front direction acute angle portion of the tip end of the emission face 64 of the fiber probe 60 is caused to be easily broken by heat, thereby shortening the life of the fiber probe 60 to which face the energy is concentrated.

Figure 12:
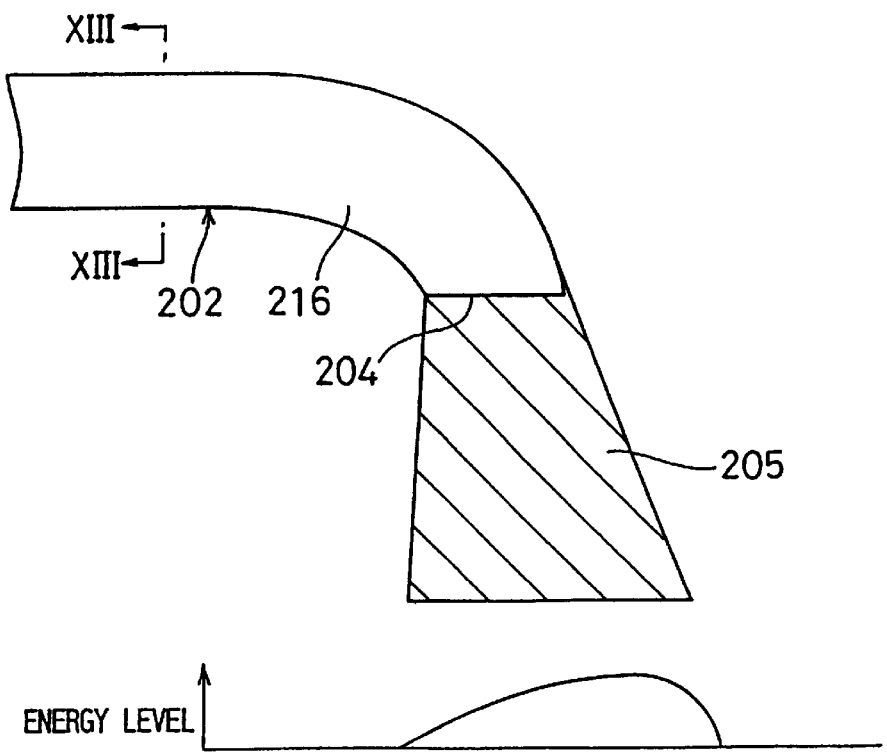
FIG. 12 is a view showing an emission pattern of a fiber probe constituted by a multifiber and a distribution of emission energy.
Figure 13:
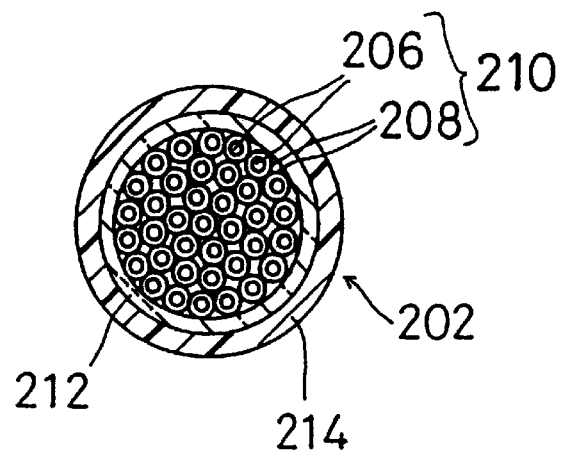
FIG. 13 is a section view taken along a line XIII—XIII in FIG. 12.

By contrast, when a multifiber 202 is used as the fiber probe 60, an emission region 205 of laser light emitted from the emission face 204 has a shape as indicated by the hatched portion in FIG. 12. As shown in FIG. 13, for example, the multifiber 202 is configured by bundling plural optical fibers 210 each consisting of a core 206 and a clad 208 which covers the core 206. The plural optical fibers 210 are bundled by, for example, a glass tube 212 so as to constitute the single fiber 202 as shown in FIG. 13. The glass tube 212 is covered by a protection tube 214 as required. When the thus constituted multifiber 202 is used, the emission face 204 of the multifiber 202 is configured as a collection of the emission faces of the optical fibers 210. Consequently, light entering the incidence faces of the optical fibers 210 travels in the respective optical fibers 210 to be emitted from the emission faces of the respective optical fibers 210, with the result that the deviation of the emitted laser light becomes small. As shown in the graph of FIG. 12, therefore, the energy of the laser light emitted from the emission face 204 is not so adversely affected by a second fiber curved part 216, and is not so ununiformly distributed in the whole of the emission face 204. As a result, a diseased part can be substantially uniformly irradiated with laser light and the durability of the fiber probe 60 is improved.

Figure 14:
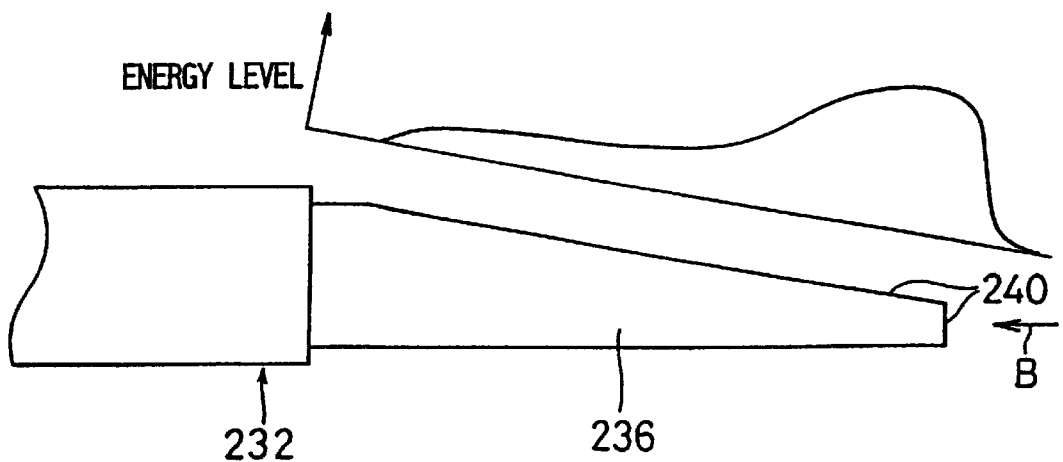
FIG. 14 is a view showing an emission pattern of another embodiment of a fiber probe consisting of a single optical fiber and a distribution of emission energy.
Figure 15:
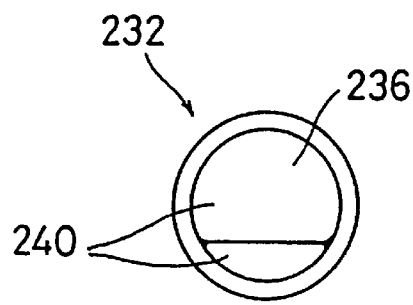
FIG. 15 is a side view as seen in the direction of an arrow B in FIG. 14.

For example, the tip end of the fiber probe may have either of the shapes shown in FIGS. 14 to 17. FIGS. 14 and 15 show a fiber probe 232 configured by a single optical fiber, and FIGS. 16 and 17 a fiber probe 234 configured by a multifiber composed of a plurality of optical fibers. In the fiber probe 232 or 234, a tapered portion 236 or 238 which extending in the axial direction in a linearly inclined manner is disposed at the tip end portion, and the inclined and end faces of the tapered portion 236 or 238 functions as an emission face 240 or 242.

The emission face 240 or 242 having such a shape may be applied to a configuration in which the whole of the fiber probe 232 or 234 extends in the axial direction in a substantially linear manner, or that in which a fiber curved part having a relatively large radius of curvature is disposed in a middle portion of the fiber probe 60*d*. An example of such configurations is the fiber probe shown in FIGS. 1 to 5.

In the case of the fiber probe 232 shown in FIGS. 14 and 15 and configured by a single optical fiber, as shown in the graph of FIG. 14, laser light emitted from the inclined emission face 240 has a tendency that the emission energy becomes larger as moving toward the tip end side of the emission face and is nonuniform in the inclination direction.

Figure 16:
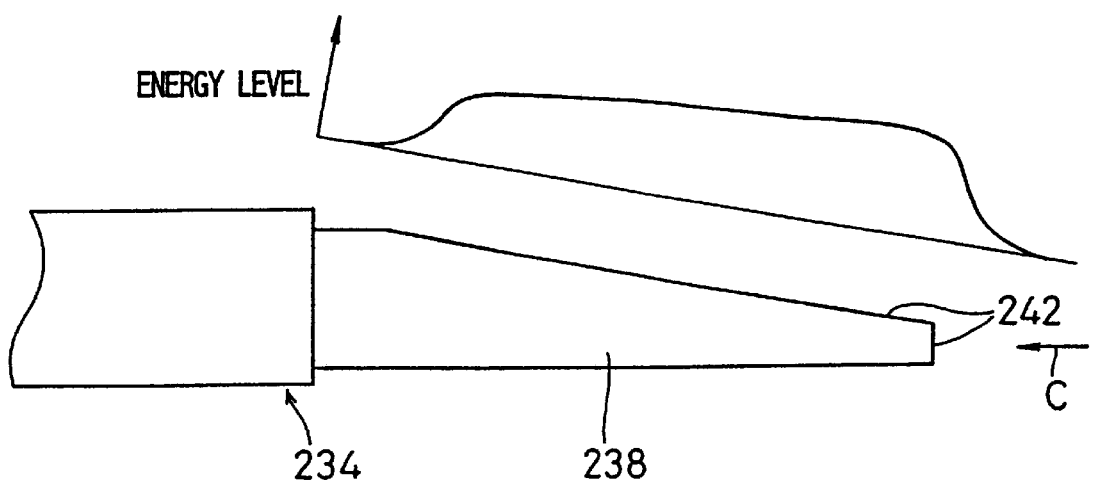
FIG. 16 is a view showing an emission pattern of another embodiment of a fiber probe constituted by a multifiber and a distribution of emission energy.
Figure 17:
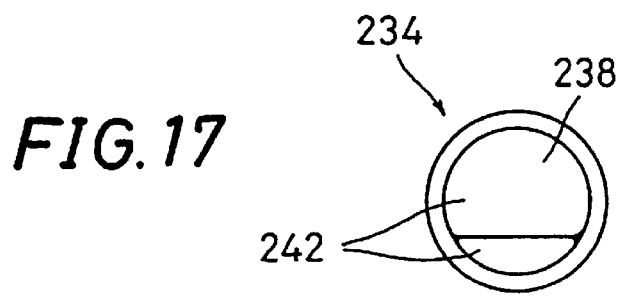
FIG. 17 is a side view as seen in a direction of an arrow C in FIG. 16.

By contrast, in the case of the fiber probe 234 constituted by a multifiber composed of a plurality of optical fibers, as shown in FIG. 16, laser light emitted from the inclined emission face 242 is substantially free from deviation in the inclination direction, and the energy distribution of the laser light is approximately uniform in the inclination direction. Therefore, a diseased part can be uniformly irradiated with laser light and the durability of the fiber probe is improved. A fiber probe of such a configuration is effective in the case where a relatively wide range is to be irradiated with laser light, and can be effectively applied to a removal of calculus in a periodontal pocket, a removal of bad granulation surface tissue, a treatment of pyorrhea alveolaris, and a disinfection treatment which is performed on a periodontal pocket by means of laser light. Depending on the contents of a treatment, there is a case where it is preferable to irradiate only a root surface or a periodontal side with laser light, such as a case where the interior of a periodontal pocket is to be irradiated with laser light. When laser light irradiation is performed uniformly and widely in a particular direction, a removal of calculus, a treatment of pyorrhea alveolaris, and the like can be uniformly performed.

Figure 18:
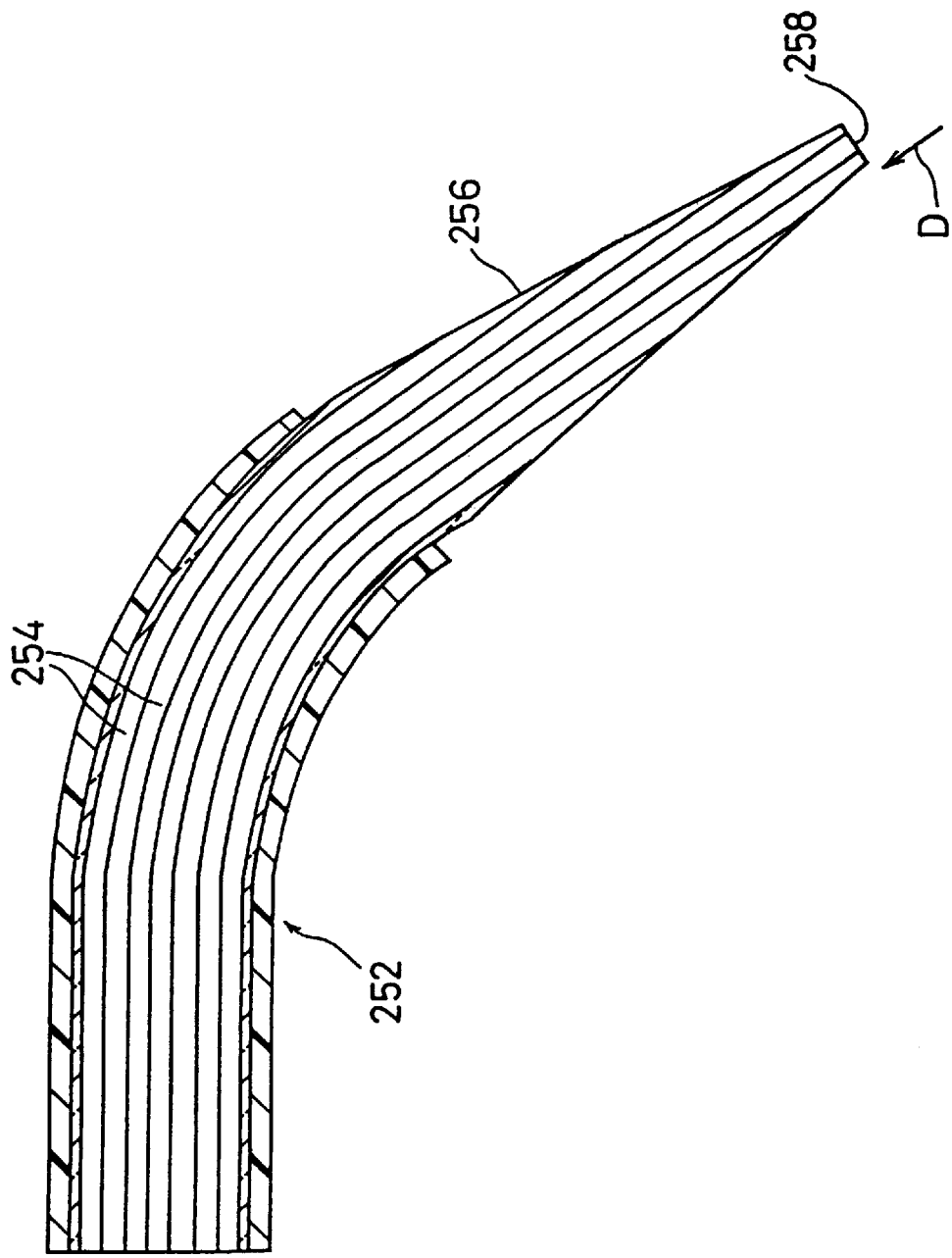
FIG. 18 is a partial enlarged section view showing a further embodiment of a fiber probe constituted by a multifiber.
Figure 19:
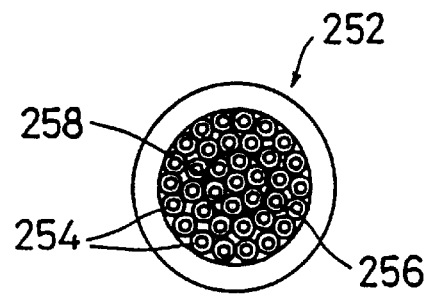
FIG. 19 is a side view as seen in a direction of an arrow D in FIG. 18.

FIGS. 18 and 19 show a further embodiment of the fiber probe.

The fiber probe 252 has a substantially same configuration as that shown in FIGS. 12 and 13 except the shape of the tip end, or is configured by a multifiber composed of a plurality of optical fibers 254. In the fiber probe 252, the tip end portion has a substantially conical shape, and a small region in the center of the tip end portion is formed into a flat circular shape. The flat region may be formed into a spherical shape.

The tip end conical face 256 and the tip end circular face 258 function as an emission face from which laser light is emitted.

When the fiber probe 252 having such a configuration is used, laser light can be substantially uniformly emitted substantially from a whole of the tip end conical face 256 of the fiber probe 252, and also from the tip end circular face 258 in the line direction.

Figure 20:
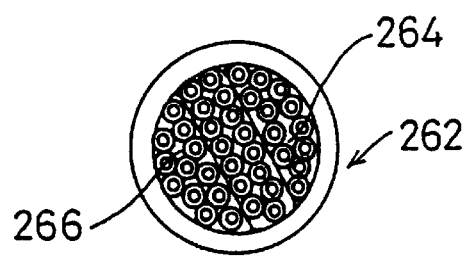
FIG. 20 is a side view showing a still further embodiment of a fiber probe, corresponding to FIG. 19.
Figure 21:
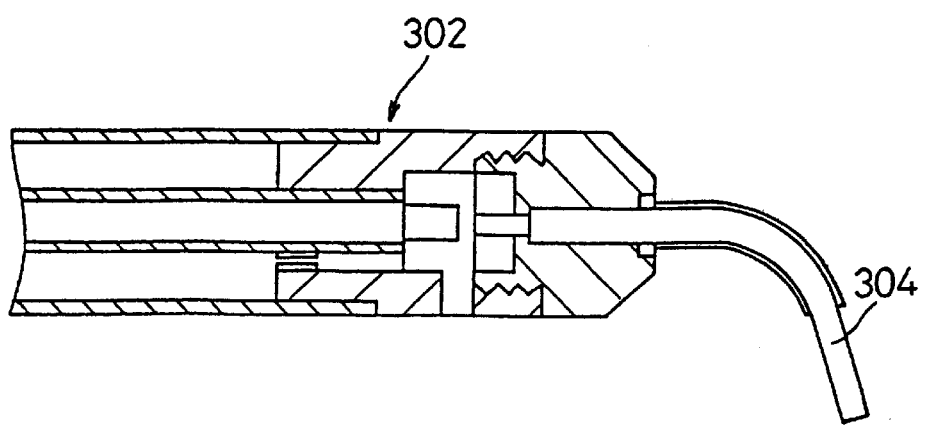
FIG. 21 is a section view showing a prior art example of fiber probe.

FIG. 20 is a view showing a still further embodiment of the fiber probe and corresponding to FIG. 19. In the embodiment, opposing peripheral faces of a fiber probe 262 are cut in a tapered manner so as to be formed into a chisel-like shape, and tapered portions 264 and 266 are disposed on the both sides.

The fiber probe 262 having such a shape can be beneficially used for simultaneously irradiating a tooth and a soft tissue of a periodontal pocket. The laser irradiation on such a wide region is effective in, for example, a removal of subgingival calculus in a periodontal pocket, a removal of infected cementum, a removal of bad granulation surface tissue, and disinfection of a periodontal pocket. Particularly, uniform irradiation enables an irradiation region to be uniformly treated.

In a laser probe configured by a single optical fiber, the tip end portion may be formed into a conical shape and the cone angle may be set to be in a range of 10 to 40°. In this case, the pattern of laser light emitted from the tip end portion of the fiber probe has a shape which is conically widened in the axial direction, and the emission energy is substantially uniform in the irradiation region. Therefore, when a circular hole is to be formed in a part of a living body, for example a thin film of a living body such as the drum membrane, laser irradiation may be performed with separating a fiber probe of such a shape from a diseased part by a given distance.

Alternatively, the tip end of a fiber probe may be formed into a semispherical shape so as to produce a lens effect. When a lens effect is provided in this way, laser light emitted from the emission face can be collected.

The embodiments described above have both the gas source and the liquid source as the fluid source. In the case where one of the sources is not required in a laser treatment, the one source may be omitted. In this case, also components such as the passage for supplying a fluid from the omitted source may be omitted.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. A medical laser treatment device comprising:
    a handpiece having a handpiece body and a laser probe to be attached to a tip end of the handpiece body;
    a laser light source for generating laser light;
    a fluid source for supplying a fluid;
    a light transmission member for guiding the laser light emitted from the laser light source to the handpiece; and
    a fluid supply passage through which the fluid is supplied from the fluid source to the handpiece body, and wherein
    the laser probe includes a fiber probe having an emission face through which the laser light from the light transmission member is emitted to an irradiation region, an annular protection tube for covering a peripheral face of the fiber probe, and a holder for holding the fiber probe and the protection tube, which holder is attached to the tip end of the handpiece body,
    between the fiber probe of the laser probe and the protection tube is defined in annular fluid passage space, through which the fluid supplied through the fluid supply passage is sprayed, the protection tube has a curved part which bends and extends with respect to an axis of the handpiece body, and the fiber probe has a first fiber curve part extending along the curved part which is formed by inserting the fiber probe into the protection tube to pass therethrough, a tip end portion of the fiber probe projects outwardly from a tip end of the protection tube, which tip end portion has a second fiber curved part disposed in the projecting tip end portion so that the emission face is directed laterally with respect to an axial direction of the tip end portion a radius of curvature (R1) of the first fiber curved part is greater than a radius of curvature (R2) of the second curved fiber part (R1>R2), and the fiber probe is constituted by a multifiber composed of a plurality of optical fibers each having a core and a clad which covers the core.

2. The medical laser treatment device of claim 1, wherein the first fiber curved part of the fiber probe is curved by 30 to 90° and extends with respect to the axis of the handpiece body, and the second fiber curved part of the fiber probe is curved in any one of a direction substantially identical with the curved direction of the first fiber curved part, a direction substantially opposite to the curved direction, and a direction substantially perpendicular to the directions.

3. The medical laser treatment device of claim 1, wherein the second fiber curved part of the fiber probe is curved so that the emission face is laterally directed.

4. The medical laser treatment device of claim 1, wherein the radius of curvature (R2) of the second fiber curved part of the fiber probe is not smaller than a diameter (D) of the fiber probe and not larger than five times (5D) the diameter of the fiber probe (5D≧R2≧D).

5. The medical laser treatment device of claim 1, wherein laser light generated by the laser light source has a wavelength of 1.0 to 5.5 µm and the fiber probe has a diameter of 0.2 to 3.0 mm.

6. A laser probe for medical laser treatment devices comprising a fiber probe for receiving laser light from a handpiece body through an incident face formed at a first end of the fiber probe and emitting the laser light from an emission face formed at a second end of the fiber probe, toward an irradiation region, and wherein the fiber probe has a fiber curved part at the second end so that the emission face is laterally directed with respect to an axis of the fiber probe, the emission face extends substantially in parallel with the axis of the fiber probe, a radius of curvature of the fiber curved part is within a range of 0.5 mm to 3.0 mm, the emission face projects from a peripheral face of the fiber probe by 0 to 3.0 mm, and the fiber probe is constituted by a multifiber composed of a plurality of optical fibers each having a core and a clad which covers the core.

7. The laser probe for medical laser treatment devices of claim 6, wherein the incidence f ace of the fiber probe has any one of a conical face, a tapered face, a semispherical face, and a flat face extending in the axial direction.

8. A laser probe for medical laser treatment devices comprising a fiber probe for receiving laser light from a handpiece body through an incidence face formed at a first end of the fiber probe and emitting the laser light from an emission face formed at a second end of the fiber probe, toward an irradiation region, and wherein the fiber probe linearly extends in an axial direction of the fiber probe in a range from the first end to a vicinity of a center portion of the fiber probe, and has a fiber curved part in a region from the vicinity of the center portion to the second end, a tapered portion in which the emission face extends in the axial direction in a linearly inclined manner and is formed in the second end of the fiber probe, and the fiber probe is constituted by a multifiber composed of a plurality of optical fibers each having a core and a clad which covers the core.

9. The laser probe for medical laser treatment devices of claim 8, wherein the incidence face of the fiber probe has any one of a conical face, a tapered face, a semispherical face, and a flat face extending in the axial direction.

10. A laser probe for medical laser treatment devices comprising a fiber probe for receiving laser light from a handpiece body through an incidence face formed at a first end of the fiber probe and emitting the laser light from an emission face formed at a second end of the fiber probe, toward an irradiation region, wherein the fiber probe linearly extends in an axial direction of the fiber probe in a range from the first end to a vicinity of a center portion of the fiber probe, and has a first fiber curved part in a region from the vicinity of the center portion to the second end, and a second fiber curved part at the second end portion of the fiber probe so that the emission face is laterally directed with respect to an axis of the second end, and a radius of curvature (R1) of the first fiber curved part is greater than a radius of curvature (R2) of the second fiber curved part (R1>R2) wherein the fiber probe is constituted by a multifiber composed of a plurality of optical fibers each having a core and a clad which covers the core.

11. The laser probe for medical treatment devices of claim 10, wherein the second fiber curved part of the fiber probe is curved in any one of a direction substantially identical with the curved direction of the first fiber curved part, a direction substantially opposite to the curved direction, and a direction substantially perpendicular to the directions.

12. The laser probe for medical treatment devices of claim 10, wherein the incidence face of the fiber probe has any one of a conical face, a tapered face, a semispherical face, and a flat face extending in the axial direction.

\* \* \* \* \*